United States Patent [19]

Lane et al.

[11] Patent Number: 5,300,198
[45] Date of Patent: Apr. 5, 1994

[54] PROCESS FOR THE SEPARATION OF ETHYLIDENE DIACETATE FROM ACETIC ANHYDRIDE

[75] Inventors: Donald W. Lane; Ronnie D. Lilly, both of Kingsport, Tenn.

[73] Assignee: Eastman Kodak Company, Rochester, N.Y.

[21] Appl. No.: 43,077

[22] Filed: Apr. 5, 1993

[51] Int. Cl.$^5$ ............................................. B01D 3/34
[52] U.S. Cl. ........................................ 203/6; 203/34; 203/91; 203/DIG. 21; 562/891; 562/898
[58] Field of Search ................. 203/91, 99, DIG. 19, 203/6, DIG. 21, 34; 528/196; 562/891, 898; 560/232

[56] References Cited

U.S. PATENT DOCUMENTS

| 4,374,070 | 2/1983 | Larkins et al. ............... 562/891 |
| 4,444,624 | 4/1984 | Erpenbach et al. ............ 203/61 |
| 4,476,238 | 10/1984 | Palmer et al. ............... 562/891 |
| 4,985,383 | 1/1991 | Erpenbach et al. ............ 560/232 |

FOREIGN PATENT DOCUMENTS 0467175  8/1950  Canada ................. 562/898

*Primary Examiner*—Virginia Manoharan
*Attorney, Agent, or Firm*—J. Frederick Thomsen; William P. Heath, Jr.

[57] ABSTRACT

A distillation process for the separation of acetic anhydride from a mixture thereof with ethylidene diacetate wherein the mixture of acetic anhydride and ethylidene diacetate is fed to the mid section of a distillation column and a small amount of acetic acid is fed separately to the lower section of the column. The addition of the acetic acid suppresses tar formation during the distillation process.

2 Claims, No Drawings

PROCESS FOR THE SEPARATION OF ETHYLIDENE DIACETATE FROM ACETIC ANHYDRIDE

This invention pertains to an improved distillation process for the separation of ethylidene diacetate from a mixture thereof with acetic anhydride. More specifically, this invention pertains to the distillation of a mixture of ethylidene diacetate and acetic anhydride in the presence of a small amount of acetic acid.

Larkin et al. U.S. Pat. No. 4,374,070 describes an improved process for the manufacture of acetic anhydride by the carbonylation of a mixture of methyl iodide and methyl acetate in the presence of a particular catalyst system. The Larkin et al. process produces a crude product which contains a small amount of ethylidene diacetate. Refining of the crude carbonylation product produces an ethylidene diacetate stream which contains a minor amount of acetic anhydride. This stream results from a final distillation to decrease the acetic anhydride fraction in the by product ethylidene diacetate to less than about 30 weight percent, preferably to less than 10 weight percent. In this final distillation step, a mixture of acetic anhydride and a minor amount of ethylidene diacetate is fed to the mid section of a conventional distillation column and a product comprising mostly acetic anhydride is removed from the top of the column. Essentially all of the ethylidene diacetate exits the column in the liquid product underflowed from the bottom of the column.

In the distillation referred to above, tar formation has been a severe problem, requiring dismantlement and cleaning or replacement of the equipment, including the column and the reboiler, column internals and piping associated therewith. The tar formation therefore occasions significant expense including cleaning costs, process down time, and/or the cost of installing duplicate equipment.

We have discovered that the above described tar formation can be decreased substantially by feeding acetic acid to the lower section, preferably to the base, of the distillation column. The improved purification process provided by our invention therefore comprises feeding (1) a mixture containing a major portion of acetic anhydride and a minor portion of ethylidene diacetate to the mid section of a distillation column and (2) acetic acid to the lower section or base of the column; and removing (A) a top product comprising mainly acetic anhydride from the upper section or top of the column and (B) a bottom product comprising mainly ethylidene diacetate from the base of the column.

The mixture subjected to the distillation may comprise about 50 to 95 weight percent acetic anhydride and 5 to 50 weight percent ethylidene diacetate with trace amounts of other materials such as acetic acid, mixed anhydrides, tars and corrosion metals. The composition of the material more typically is about 80 to 95 weight percent acetic anhydride and 5 to 20 weight percent ethylidene diacetate.

The amount of acetic acid fed separately to the lower section or base of the distillation column normally should be approximately 1 weight percent of the weight of the acetic anhydride/ethylidene diacetate mixture fed. The practical upper limit of acetic acid is believed to be about 10 weight percent of the weight of the acetic anhydride/ethylidene diacetate mixture fed since feeding excessive amounts of acetic acid produces no additional benefits but only places an additional load on the column. The addition of the acetic acid to the lower section, most preferably to the base, of the column is an important feature of the invention. The addition of acetic acid above the lower section or base of the distillation column does not achieve the degree of tar suppression afforded by our invention.

The purity of the acetic anhydride removed from the top of the column and the ethylidene diacetate removed from the bottom of the column can be varied significantly depending on the number of stages and the amount of reflux used. The design purity of these streams depend on the particular economic factors for a given installation and are not conditions for this particular invention. In other words, the addition of acetic acid to the base of the distillation column will reduce the amount of tar formed regardless of the temperature, pressure or product specifications for the distillation.

The distillation may be carried out over a wide range of temperatures and pressures. For example, column top temperatures of about 75° to 140° C. and absolute pressures of 100 torr to ambient pressure may be used, depending on the design of a particular installation.

In one particular installation, the acetic anhydride obtained from the distillation process of the present invention generally contains less than 2 weight percent ethylidene diacetate but the percentage can be controlled as low as 0.2 weight percent if desired. The composition of the underflow stream typically is in the range of about 70 to 95 weight percent ethylidene diacetate and 5 to 30 weight percent acetic anhydride with up to about 2 weight percent acetic acid.

The weight percent ethylidene diacetate in the column bottom product is limited by the amount of tar formed in the column. In general, if the ethylidene diacetate concentration increases, more tar is formed and the product becomes more viscous. The column operation usually is then changed to cause more acetic anhydride to leave the bottom of the column to dilute the tar and lower the viscosity of the bottom product. Thus, the acetic acid addition in accordance with our invention also permits the concentration of ethylidene diacetate in the underflow to be increased since less tar will be formed when the invention is used. The novel process described herein can be carried out in conventional distillation equipment comprising a column containing trays or packing materials, feed lines, take-off lines and a heat source such as a reboiler to provide the necessary process heat.

The improved distillation process of this invention is further illustrated by the following example wherein flow rates are given in parts by weight and stream compositions are given in percentages by weight. A mixture containing 90 weight percent acetic anhydride, 10 weight percent ethylidene diacetate and traces of lower and higher boiling components was fed to approximately the mid point of the side of a commercially operated distillation column at the rate of 10 parts per hour. A separate stream of acetic acid was fed to the base of the column at a rate of 1 parts per hour. The temperature and pressure at the column top were maintained at approximately 78° C. and 100 torr and at 125° C. at and 300 torr at the base of the column.

Acetic anhydride containing less than 2 weight percent ethylidene diacetate was removed as a distillate from the top of the column at a rate of slightly less than 9 parts per hour. The approximate average composition of the underflow was 80% ethylidene diacetate, 10% acetic anhydride, 1% percent acetic acid and 9% of other components including tars. After 7 days of operation, there was no evidence of fouling. However, when the acetic acid feed was stopped, the reboiler fouled with tars within a few (2 or 3) days. After cleaning the reboiler, the column was restarted with the same feeds as described above except that the acetic acid feed to the base gradually was reduced (over a period of a few days) to 0.1 part per hour and maintained at a flow rate of 0.1 part per hour. Operation of the column in this manner was continued for 16 days and then terminated. The distillation equipment was found to be much cleaner when compared with previous operations without any acetic acid feed to the base of the column. The reboiler was cleaned during this shutdown and operation of the column was restarted but without the acetic acid feed to the base. The result was fouling of the reboiler after only 3 days operation requiring shut down and cleaning of the column. These tests confirmed that tar fouling is reduced by feeding acetic acid to the base of the column.

The invention has been described in detail with particular reference to preferred embodiments thereof, but it will be understood that variations and modifications can be effected within the spirit and scope of the invention.

We claim:

1. Process for the separation of acetic anhydride from ethylidene diacetate which comprises feed (1) a mixture comprising about 50 to 95 weight percent acetic anhydride and 5 to 50 weight percent ethylidene diacetate to the mid-section of a distillation column and (2) acetic acid to the base of the column; and removing (A) a top product comprising acetic anhydride containing less than 2 weight percent ethylidene diacetate from the top of the column and (B) a bottom product comprising bout 70 to 95 weight percent ethylidene diacetate, 5 to 30 weight percent acetic anhydride, and up to about 2 weight percent acetic acid from the base of the column; wherein the distillation is carried out at a column top temperature in the range of about 75° to 140° C. and at a pressure of about 100 torr to atmospheric pressure and the amount of acetic acid fed is about 1 to 10 weight percent based on the weight of mixture of acetic anhydride an ethylidene diacetate fed whereby tar formation is decreased.

2. Process for the separation of acetic anhydride from ethylidene diacetate which comprises feeding (1) a mixture comprising about 80 to 95 weight percent acetic anhydride and 5 to 20 weight percent ethylidene diacetate to the mid-section of a distillation column and (2) acetic acid to the base of the column; and removing (A) a top produce comprising acetic anhydride containing less than 2 weight percent ethylidene diacetate from the top of the column and (B) a bottom product comprising about 70 to 95 weight percent ethylidene diacetate, 5 to 30 weight percent acetic anhydride, and up to about 2 weight percent acetic acid from the base of the column; wherein the distillation is carried out at a column top temperature in the range of about 75° to 140° C. and at a pressure of about 100 torr to atmospheric pressure and the amount of acetic acid fed is about 1 to 10 weight percent based on the weight of the mixture of acetic anhydride/ethylidene diacetate fed whereby tar formation is decreased.

* * * * *